United States Patent [19]

Wegner et al.

[11] Patent Number: 5,310,551

[45] Date of Patent: May 10, 1994

[54] METHOD FOR INHIBITING PULMONARY OXYGEN TOXICITY

[75] Inventors: Craig D. Wegner, New Milford; L. Gordon Letts, Newtown, both of Conn.

[73] Assignee: Boehringer Ingelheim Pharmaceuticals, Inc., Ridgefield, Conn.

[21] Appl. No.: 15,744

[22] Filed: Feb. 10, 1993

Related U.S. Application Data

[63] Continuation of Ser. No. 679,870, Apr. 3, 1991, abandoned.

[51] Int. Cl.$^5$ .................. A61K 39/00; A61K 39/395; C07K 15/28
[52] U.S. Cl. ........................ 424/85.8; 530/388.22; 530/388.73; 530/389.6
[58] Field of Search ............... 424/85.8, 88; 514/2, 514/8, 12, 886; 530/395, 388.22, 388.73, 389.6

[56] References Cited

U.S. PATENT DOCUMENTS 5,109,123  4/1992  Reinherz et al. .................. 536/27

OTHER PUBLICATIONS

Barton et al., J. Immunol. 143:1278-1282 (1989) "The effect of anti-intercellular adhesion molecule-1 on phorbol-ester-induced rabbit lung inflammation".
Gallin, J. I. in *Fundamental Immunology* (W. F. Paul, (ed)) Ch. 26, pp. 721-733 (1989), "Inflammation".
Ruoslahti, et al. in *Syn. Peptides in Biology and Medicine*, pp. 191-197 (1985) "Synthetic peptides in analysis of cell adhesion".
Shevach, et al. in *Fundamental Immunology* (W. F. Paul (ed.)) Ch. 15, pp. 413-422, 437-438 (1989) "Accessory molecules".
Wegner et al., Science 247:456-459 (Jan. 20, 1990), "Intercellular adhesion molecule-1 (1 ICAM-1) in the pathogenesis of asthma".

*Primary Examiner*—Christine M. Nucker
*Assistant Examiner*—Thomas Cunningham
*Attorney, Agent, or Firm*—Sterne, Kessler, Goldstein & Fox

[57] ABSTRACT

A method for inhibiting pulmonary oxygen toxicity in a patient requiring elevated levels of inhaled oxygen, by prophylactic administration of certain adhesion molecules and antibodies thereto.

2 Claims, No Drawings

METHOD FOR INHIBITING PULMONARY OXYGEN TOXICITY

This is a continuation of application Ser. No. 679,870, filed Apr. 3, 1991, now abandoned.

FIELD OF THE INVENTION

This invention relates to a method for inhibiting pulmonary oxygen toxicity in a patient requiring elevated levels of inhaled oxygen. More particularly, this invention relates to a method for inhibiting pulmonary oxygen toxicity utilizing certain adhesion molecules and antibodies thereto.

BACKGROUND OF THE INVENTION

Certain conditions, such as bypass surgery, trauma, head injuries, emboli, septic shock, pneumonia, smoke inhalation and premature birth, can result in lung edema and impaired alveolar gas exchange. In such patients, the use of elevated levels of inhaled oxygen is necessary to achieve acceptable blood oxygen saturation. However, prolonged exposure to greater than 0.5 atmospheres of oxygen can result in lung injury, edema, fibrosis, and, eventually death. Methods for inhibiting the toxic effects of such elevated levels of inhaled oxygen are, therefore, desirable.

Results from investigations with laboratory animals have led to a three phase hypothesis for the pathogenesis of pulmonary oxygen toxicity. During the first or initiation phase (24 to 48 hours at 1 atmosphere of inhaled oxygen), reactive oxygen radicals are generated within alveolar cells causing endothelial lactate dehydrogenase (LDH) release, macrophage release of a neutrophil chemotactic factor, epithelial damage, very mild extravascular leakage of fluid and chest stiffness. The second, amplification or inflammation, phase (72 to 96 hours at 1 atmosphere of inhaled oxygen) is characterized by a massive neutrophil infiltration, marked endothelial, epithelial and surfactant damage, moderate pulmonary edema, and mild to moderate respiratory distress or "ill feeling". During the third or destructive phase, these effects resolve within additional days (1 to 7) in death or within months (1 to 3) in pulmonary fibrosis. See, e.g., Crapo, J. D., Ann. Rev. Physiol. 48: 721 (1986).

Certain cytotoxic agents have been shown to reduce circulating and tissue neutrophils. These cytotoxic agents, however, cannot be used as therapies in humans. Furthermore, reducing circulating and tissue neutrophils does not necessarily prevent lung injury due to hypoxia. For example, Shasby et al, J. Appl. Physiol. 52:1237–1244 (1982) describe findings using nitrogen mustard that suggest that granulocytes may contribute to production of edema in acute oxygen toxicity. Suttrop et al, J. Clin. Invest. 70:342–350 (1982), describe findings using SOD, inter alia, that indicate that the increase in susceptibility of lung cells to neutrophil-mediated oxidant damage is an effect of hyperoxia on lung cells. Parrish et al, J. Clin. Invest. 74:956–965 (1984), describe early accumulation of neutrophils in oxygen toxicity, particularly in C5-sufficient mice. Krieger et al, J. Appl. Physiol. 58:1326–1330 (1985), describe findings suggesting that the synergistic interaction between hyperoxia and granulocytes in producing acute lung injury involves a primary effect of hyperoxia on the lung itself. Laughlin et al, J. Appl. Physiol. 61:1126–1131 (1986), concluded that neutrophils do not play a significant role during the early stages of sublethal hyperoxic injury to rabbit alveolar epithelium. Smith et al, J. Lab Clin. Med. 111(4): 449–458(1988), describe results indicating that PMNs are not required for either the development or progression of hyperoxic lung damage in mice. Das et al, Biomed. Biochim. Acta 47(12):1023–1036 (1988), describe a study demonstrating that ibuprofen cannot prevent hyperoxic lung injury although it inhibits the influx of PMN into the injured lung, suggesting that PMN are not directly involved in the injury process.

Neutrophils are one group of white blood cells whose diapedesis is controlled by cellular adhesion. Cellular adhesion is a process through which leukocytes attach to cellular substrates, such as endothelial cells, in order to migrate from circulation to sites of ongoing inflammation, and properly defend the host against foreign invaders such as bacteria or viruses. An excellent review of the defense system is provided by Eisen, H. W., (In: Macrobiology, 3rd Ed., Harper & Row, Philadelphia, pA (1980), pp. 290-295 and 381-418).

One of the molecules on the surface of endothelial cells which participates in the adhesion process is the intercellular adhesion molecule ICAM-1. See Rothlein et al, J. Immunol. 137:1270 (1986), (hereinafter referred to as ("Rothlein et al"). This molecule has been shown to mediate adhesion by binding to molecules of the CD18 family of glycoproteins which are present on the cell surfaces of leukocytes (Sanchez-Madrid, F. et al., J. Exper. Med 158:1785–1803 (1983); Keizer, G. D. et al., Eur. J. Immunol. 15:1142–1147 (1985)). This glycoprotein family is composed of heterodimers having one alpha chain (also referred to as "CD11") and one beta chain (also referred to as "CD18"). There are three major members of the CD18 family: p150,95, Mac-1 and LFA-1. Mac-1 is a heterodimer found primarily on macrophages, granulocytes and large granular lymphocytes. LFA-1 is a heterodimer found on most lymphocytes (Springer, T. A., et al. Immunol. Rev. 68:111–135 (1982)). p150,95 has a tissue distribution similar to Mac-1, and also plays a role in cellular adhesion (Keizer, G. et al., Eur. J. Immunol. 15:1142–1147 (1985)).

Mouse monoclonal antibodies to human ICAM-1 have been shown to inhibit lymphocyte proliferative responses requiring cell/cell interactions as well as inhibiting granulocyte attachment and subsequent migration through endothelial cell monolayers in vitro. Anti-ICAM-1 antibodies are also known to inhibit leukocyte migration to inflamed lungs in rabbits, kidney allograft rejection and antigen-induced airway hyperreactivity in primates. See, e.g., Dustin et al J. Immunol. 137:245 (1986) Barton et al, J. Immunol. 143:1278 (1989), Cosimi et al., J. Immunol. 144:4604 (1990) and Wegner et al, Science 247:456 (1990).

Anti-CD18 antibodies have been described as useful in treating hemorrhagic shock in rabbits. Vedder et al, J. Clin, Invest. 81: 939 (1988). Anti-CD18 antibodies have been shown not to increase susceptibility to sepsis when used to inhibit neutrophil adherence in rabbits. Mileski et al, Surgical Forum, Infection and its Mediators, p. 107 (1989).

Accordingly, it is the purpose of this invention to provide a novel method for inhibiting pulmonary oxygen toxicity in a patient requiring elevated levels of inhaled oxygen, using an adhesion molecule or antibody thereto.

DESCRIPTION OF THE INVENTION

This invention relates to a method for inhibiting pulmonary oxygen toxicity in a patient susceptible thereto which comprises prophylactically administering to the patient an effective amount of an agent selected from the group consisting of:
- a) an antibody capable of binding to ICAM-1;
- b) a fragment of the antibody (a), the fragment being capable of binding to ICAM-1;
- c) ICAM-1, being substantially free of natural contaminants;
- d) a functional derivative of ICAM-1;
- e) an antibody capable of binding to a member of the CD18 family of glycoproteins;
- f) a fragment of the antibody (e), the fragment being capable of binding to a member of the CD18 family of glycoproteins;
- g) a member of the CD18 family of glycoproteins, being substantially free of natural contaminants; and
- h) a functional derivative of a member of the CD18 family of glycoproteins.

Preferably, the agent is an antibody, or fragment thereof, capable of binding to ICAM-1.

Pulmonary oxygen toxicity for the purpose of this invention is defined as the acute lung injury (dysfunction) and chronic lung scarring (fibrosis), or death due to lung dysfunction, caused by oxygen inhalation. Pulmonary oxygen toxicity results from inhalation of elevated levels of oxygen, generally greater than 0.5 atm for greater than 24 hours.

As used herein, a molecule is a member of the CD18 family of glycoproteins if it contains either an alpha subunit of a member of the CD18 family of glycoproteins (i.e. a CD11 subunit), a beta subunit of a member of the CD18 family of glycoproteins (i.e. a CD18 beta subunit), or both an alpha and a beta subunit of a member of the CD18 family of glycoproteins. Thus, as used herein, a member of the CD18 family of glycoproteins includes molecules having only one subunit of a CD18 member as well as heterodimer (i.e. a molecule having both an alpha and a beta subunit of a member of the CD18 family. All such molecules may be either bound to a membrane or solid support or unbound (i.e. "soluble").

"ICAM-1" is the natural ligand for the CD18 family of glyooprotein receptor molecules (Rothlein et al; Marlin et al., Cell 51:813 (1987)). ICAM-1 is a 76–97 Kd glycoprot®in. ICAM-1 is not a heterodimer. The identification, characterization, and amino acid sequence of ICAM-1, and the production of antibody reactive with ICAM-1 and other adhesion molecules are disclosed in and in Rothlein et al; Smith et al., in *Structure and Function of Molecule Involved in Leukocyte Adhesion*, A. S. Rosenthal, et al., Eds. (Springer-Verlag, N.Y., 1989); Smith, J. Clin. Invest. 82:1746 (1988) and Barton et al, J. Immunol. 143 (1989)).

A "functional derivative" of ICAM-1 is a compound which possesses a biological activity (either functional or structural) that is substantially similar to a biological activity of ICAM-1. The term "functional derivatives" is intended to include the "fragments", "variants", "analogs", or "chemical derivatives" of a molecule. A "fragment" of a molecule such as ICAM-1, is meant to refer to any polypeptide subset of the molecule. Fragments of ICAM-1 which have ICAM-1 activity and which are soluble (i.e. not membrane bound) are especially preferred.

A "variant" of a molecule such as ICAM-1 is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess similar activity, they are considered variants as that term is used herein even if the structure of one of the molecules not found in the other, or if the sequence of amino acid residues is not identical. An "analog" of a molecule such as ICAM-1 is meant to refer to a molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Science* (16th ed., Osol, A. Ed., Mack, Easton PA (1980)).

Of interest to the present invention are functional derivatives of LFA-1, Mac-1 or p150,95 which are soluble molecules. Of special interest are functional derivatives of these molecules which are heterodimers (containing both the alpha and beta subunits of the molecules) and monomeric derivatives capable of binding ICAM-1. Soluble heterodimers are especially preferred.

ICAM-1 and the members of the CD18 family of molecules are immunogenic molecules. Thus, it is possible to obtain antibodies capable of binding to ICAM-1 or members of the CD18 family of molecules. Such antibodies may be used in accordance with the method of the present invention.

Such antibodies may be obtained by introducing either the purified molecules (or cells which naturally express these molecules) into an appropriate animal, as by intraperitoneal injection, etc. If desired, the serum of such an animal may be removed and used as a source of polyclonal antibodies capable of binding these molecules. It is, however, preferable to remove splenocytes from such animals, to fuse such spleen cells with a myeloma cell line and to permit such fusion cells to form hybridoma cells which secrete monoclonal antibodies capable of binding ICAM-1 or members of the CD18 family of molecules.

The hybridoma cells, obtained in the manner described above, may be screened as described above to identify desired hybridoma cells that secrete antibody capable of binding either to ICAM-1 or to members of the CD18 family of molecules (either the alpha or beta subunit).

As indicated above, both polyclonal and monoclonal antibodies may be employed in accordance with the present invention. Of special interest to the present invention are antibodies to ICAM-1 (or their functional derivatives), which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson et al, International Patent Publication PCT/US86/02269; Akira et al, European Patent Application 184,187; Taniguchi, European Patent Application 173,494; Neuberger, PCT Application WO 86/01533; U.S. Pat. No. No. 4,816,397; Better et al, Science 240:1041-1043 (1988); Liu et al, Proc. Natl. Acad. Sci. USA 84:3439-3443 (1987); Liu, J. Immunol. 139:3521-3526 (1987); Sun, Proc. Natl. Acad. Sci. USA 84:214-218 (1987); Nishimura et al, Canc. Res. 47:999-1005 (1987); Wood et al, Nature 314:446-449 (1985)); Shaw et al, J. Natl. Cancer Inst. 80:1553-1559 (1988).

General reviews of "humanized" chimeric antibodies are provided by Morrison (*Science*, 229:1202-1207 (1985)) and by Oi et al. BioTechniques 4:214 (1986)).

Suitable "humanized" antibodies can be alternatively produced by CDR or CEA substitution (Jones et al, Nature 321:522-525 (1986); Verhoeyan et al, Science 239:1534 (1988); Beidler et al, J. Immunol. 141:4503-4060 (1988)).

The agents useful in the method of the present invention may be obtained by natural processes (such as, for example, by inducing an animal, plant, fungi, bacteria, etc., to produce a non-immunoglobulin antagonist of ICAM-1, or by inducing an animal to produce polyclonal antibodies capable of binding to ICAM-1); by synthetic methods (such as, for example, by using the Merrifield method for synthesizing polypeptides to synthesize ICAM-1, functional derivatives of ICAM-1, or protein antagonists of ICAM-1 (either immunoglobulin or non-immunoglobulin)); by hybridoma technology (such as, for example, to produce monoclonal antibodies capable of binding to ICAM-1); or by recombinant technology (such as, for example, to produce the agents of the present invention in diverse hosts (i.e., yeast, bacteria, fungi, cultured mammalian cells, etc.), or from recombinant plasmids or viral vectors), or by proteolysis. The choice of which method to employ will depend upon factors such as convenience, desired yield, etc. It is not necessary to employ only one of the above described methods, processes, or technologies to produce a particular agent; the above described processes, methods, and technologies may be combined in order to obtain a particular agent.

Several methods for administering the agents useful in the method of this invention to the patient can be used including, for example, intradermal, subcutaneous, intramuscular, intraperitoneal, intravenous, intranasal, and by oral inhalation. Preferably, the agent is administered by intravenous injection.

In providing a patient with the agent useful in the method of this invention, the dosage of administered agent, will vary depending upon such factors as the patient's age, health, duration of exposure, barometric pressure of the inhaled gas mixture, composition of inhaled gases, $P_aO_2$, etc. In general, it is desirable to provide the patient with a dosage of administered agent in the range of from about 0.1-10.0 mg/kg (body weight of patient), although a lower or higher dosage may be administered.

The agent useful in the method of this invention, is administered prophylactically, i.e., in advance of the onset of pulmonary oxygen toxicity. The prophylactic administration of the agent, serves to inhibit or attenuate any subsequent toxic response to the oxygen.

The agent can be administered in a single prophylactic dose or in multiple prophylactic doses. Multiple doses can be administered at regular intervals during the period of time that the patient is exposed to the elevated level of inhaled oxygen and for a brief period (1-3 days) thereafter.

The agent useful in the method of this invention can be formulated according to known methods to prepare pharmaceutically useful compositions, whereby the agent is combined in admixture with a pharmaceutically acceptable carrier. Suitable vehicles and their formulations are described, for example, in *Remington's Pharmaceutical Sciences* (16th ed., Osol, A, Ed., Mack, Easton PA (1980)).

The following example is an illustration of the present invention.

EXAMPLE I

A. Preparation of Monoclonal Antibodies

The antibody YN1/1.7 is a rat anti-mouse ICAM-1 monoclonal antibody which was prepared as described in Takei et al, J. Immunology 134:1403 (1985).

The antibody M18/2a is a rat anti-mouse CD18 monoclonal antibody which was prepared as described in Sanchez-Madrid et al., J. Exp. Med. 158:586 (1983).

B. Preparation of Mice

Male Balb-c mice (Charles River Labs, Cambridge, MA), 8 to 10 weeks old, weighing 20-25 grams were housed on wire mesh above bedding in chambers placed in a fume hood. Food and water were supplied ad libitum. The mice were exposed to oxygen as described below.

1. Control group mice were exposed to 100% oxygen at 1 atmosphere for up to 84 hours to determine the time course of lung toxicity. At specific time points (0, 24, 48, 72 and 84 hours), six mice were removed and tested. Each removed mouse was anesthetized with 100mg/kg, i.p. nembutal and a tracheal cannula was inserted. Lung compliance and resistance were determined by discrete frequency forced ocillations according to the procedure described in Wegner et al, Respir. Physio. 55:47 (1984) and Kotlikoff et al, J. Appl. Physiol. 56:182 (1984). Lung diffusion capacity was determined by the carbon monoxide single breath method described in Forster et al, J. Clin. Invest. 33:1135 (1954). Alveolar cell composition and protein were assayed by whole lung lavage as described in Hunninghake et al, Ana J. Path. 97:144 (1979). Serum for lactate dehydrogenase (LDH) activity was obtained by cardiac puncture and LDH activity was then determined as described in Wroblewski et al, Proc. Soc. Exp. Biol. Med. 90:210 (1955). The mice were then terminated by cervical dislocation.

The results are summarized in Table 1 below.

2. A control group and a first treated group were exposed to either i) 90-95% oxygen for 84 hours at 1 atmosphere or ii) ≧95% oxygen for 60 hours followed by 21% (atmospheric) oxygen for 48 hours at 1 atmosphere. A second treated group was exposed to 90-95% oxygen for 84 hours at 1 atmosphere. The control group was treated with saline by intraperitoneal injection at the beginning of the exposure and then every six (6) (for i) and twelve (12) (for ii), hours thereafter. The first treated group was treated with YN1/1.7 (3mg/kg for i or 10 mg/kg for ii) by intraperitoneal injection at the beginning of the exposure and every twelve (12) hours thereafter. The second treated group was tested with M18/2a (3mg/kg) at the beginning of the exposure and every six (6) hours thereafter. At the end of each respective time period, the mice were removed and tested as described above for the control group described above in 1.

These results are summarized in Table 2 below c. RESULTS

TABLE 1

| | | TIME COURSE OF PULMONARY OXYGEN TOXICITY IN MICE | | | | |
|---|---|---|---|---|---|---|
| HOURS OF | PLASMA | LUNG LAVAGE | | | | |
| $O_2$ Exposure | LDH (units/l) | LDH (units/l) | #PMN'S ($\times 10^3$/ml) | Protein (units/ml) | Crs ($\mu$l/cm H2O) | $D_{LCO}$ ($\mu$l/min/mmHg) |
| 0 | 175 ± 21 | 51 ± 6 | 3 ± 1 | 153 ± 27 | 13.0 ± 0.6 | 15.4 ± 1.2 |
| 24 | 214 ± 23 | 80 ± 14 | 12 ± 5 | 230 ± 47 | 13.9 ± 1.4 | 17.5 ± 2.2 |
| 48 | 416 ± 34 | 107 ± 21 | 15 ± 8 | 227 ± 45 | 14.9 ± 1.4 | 12.3 ± 0.4 |
| 72 | 544 ± 72* | 102 ± 4 | 24 ± 9* | 343 ± 31 | 9.2 ± 1.2* | 10.4 ± 0.2* |
| 84 | 811 ± 40* | 233 ± 42* | 63 ± 38* | 1413 ± 120 | — | 5.1 ± 0/4* |

Abbreviations:
LDH = lactate dehydrogenase;
PMN = polymorphonuclear leukocytes (neutrophils);
Crs = respiratory system compliance;
$D_{Lco}$ = diffusion capacity of the lungs for carbon monoxide
*p < 0.05 versus no exposure (0 hours), Dunnett's t-test.
All values are mean ± S.E.M. (N = 5 − 6).

Lung function remained unchanged over the first 48 hours of exposure and then deteriorated rapidly after 72 hours of exposure. Neutrophil infiltration was noticeable at 72 hours but still only mild at 84 hours when the deterioration in lung function and onset of labored breathing were marked and rapidly progressing.

TABLE 2

| | | EFFECTS OF ANTI-ICAM-1 AND ANTI-CD18 ON PULMONARY OXYGEN TOXICITY IN MICE | | | | |
|---|---|---|---|---|---|---|
| Exposure time | Treatment | LDH (u/l) | #PMN's ($\times 10^3$/ml) | Protein (u/ml) | Crs ($\mu$l/cmH$_2$O) | $D_{Lco}$ ($\mu$l/min/mmHg) |
| 0 | — | 86 ± 9 | 9 ± 1 | 409 ± 32 | 31.8 ± 2.0 | 18.6 ± 0.8 |
| 84 | Saline | 246 ± 14 | 44 ± 13 | 1573 ± 133 | 8.9 ± 0.7 | 10.3 ± 0.5 |
| 84 | YN1/1.7 | 193 ± 9* | 21 ± 4 | 1284 ± 154 | 13.2 ± 1.0* | 12.0 ± 0.5 |
| 84 | M18/2a | 209 ± 19 | 16 ± 2* | 1355 ± 156 | 11.2 ± 0.9 | 11.3 ± 0.4 |
| 60 | Saline | 111 ± 8 | 58 ± 18 | 721 ± 50 | 24.3 ± 1.7 | 13.8 ± 0.8 |
| 60 | YN1/1.7 | 98 ± 6 | 41 ± 1 | 613 ± 30 | 32.6 ± 2.3* | 17.0 ± 0.6* |

Abbreviations:
LDH = lactate dehydrogenase;
PMN = polymorphonuclear leukocytes (neutrophils);
Crs = respiratory system compliance;
$D_{Lco}$ = diffusion capacity of the lungs for carbon monoxide
*p < 0.05: significant protection of treatment with anti-adhesion protein monoclonal antibody versus saline; Dunnett's t-test.
All values are mean ± S.E.M. (N = 5-6).

YN1/1.7 provided significant protection against the oxygen induced increase in lung damage (lung lavage LDH) and dysfunction (decrease in Crs) in the 84 hour exposure as well as the lung dysfunction (reduction in Crs and $D_{LCO}$) in the milder 60 hour exposure.

M18/2a inhibited the oxygen-induced neutrophil infiltration and inhibited changes in lung LDH and function.

What is claimed is:

1. A method for reducing the severity of pulmonary oxygen toxicity in a patient susceptible thereto, which comprises prophylactically administering to the patient an agent selected from the group consisting of:
    a) an antibody capable of interfering with ICAM-1-dependent adhesion, by binding to ICAM-1; and
    b) a fragment of antibody (a), the fragment being capable of interfering with ICAM-1 dependent adhesion, by binding a ICAM-1.
2. The method of claim 1 wherein the antibody (a) is a monoclonal antibody.